United States Patent [19]

Bournonville et al.

[11] Patent Number: 5,268,522

[45] Date of Patent: * Dec. 7, 1993

[54] PROCESS FOR THE AROMATIZATION OF HYDROCARBONS CONTAINING 5 TO 9 CARBON ATOMS PER MOLECULE IN THE PRESENCE OF A PARTICULAR CATALYST

[75] Inventors: Jean-Paul Bournonville, Cergy Pontoise; Francis Raatz, Saint Avold; Jeannine Juguin, Rueil Malmaison; Sylvie Juguin, Aucamville, all of France

[73] Assignee: Institut Francais du Petole, Rueil Malmaison, France

[*] Notice: The portion of the term of this patent subsequent to Jul. 13, 2010 has been disclaimed.

[21] Appl. No.: 965,548

[22] Filed: Oct. 23, 1992

Related U.S. Application Data

[63] Continuation of Ser. No. 752,370, Sep. 3, 1991, abandoned.

[30] Foreign Application Priority Data

Sep. 3, 1990 [FR] France ................... 90 10947

[51] Int. Cl.$^5$ ............................................. C07C 15/00
[52] U.S. Cl. .................... 585/415; 585/407; 585/418; 585/419
[58] Field of Search ............... 585/407, 415, 418, 419

[56] References Cited

U.S. PATENT DOCUMENTS

| | | |
|---|---|---|
| 4,036,741 | 7/1977 | Pollitzer et al. . |
| 4,072,731 | 2/1978 | Rausch . |
| 4,214,980 | 7/1980 | Le Page et al. . |
| 4,497,969 | 2/1985 | Ball et al. ............... 585/415 |
| 4,590,322 | 5/1986 | Chu . |
| 4,766,265 | 8/1988 | Desmond et al. ......... 585/419 |
| 4,806,699 | 2/1989 | Smith et al. . |
| 4,808,763 | 2/1989 | Shum ........................ 585/417 |
| 4,839,320 | 6/1989 | Trowbridge et al. . |
| 4,861,740 | 8/1989 | Sachtler et al. . |
| 4,861,934 | 8/1989 | Suzuki et al. ............ 585/418 |
| 4,886,927 | 12/1989 | Sachtler et al. . |
| 4,922,051 | 5/1990 | Nemet-Mavrodin et al. . |
| 4,923,835 | 5/1990 | Travers et al. . |
| 5,010,048 | 4/1991 | Petit et al. . |
| 5,026,921 | 6/1991 | Degnan, Jr. et al. ....... 585/418 |
| 5,073,673 | 12/1991 | Hirabayashi et al. ...... 585/418 |

FOREIGN PATENT DOCUMENTS

| | | |
|---|---|---|
| 754019 | 1/1971 | Belgium . |
| 47-42254 | 10/1972 | Japan . |
| 7001852 | 8/1969 | Netherlands . |

*Primary Examiner*—Patrick P. Garvin
*Assistant Examiner*—E. D. Irzinski
*Attorney, Agent, or Firm*—Millen, White, Zelano & Branigan

[57] ABSTRACT

For the catalytic aromatization of hydrocarbons containing 5 to 9 carbons atoms per molecule, use is made of a catalyst containing a MFI zeolite containing at least one noble metal from the platinum family and at least one additional metal chosen from the group constituted by tin, germanium, lead and indium, and optionally an amorphous matrix.

14 Claims, No Drawings

PROCESS FOR THE AROMATIZATION OF HYDROCARBONS CONTAINING 5 TO 9 CARBON ATOMS PER MOLECULE IN THE PRESENCE OF A PARTICULAR CATALYST

This application is a continuation of application Ser. No. 07/752,370, filed Sep. 3, 1991 and now abandoned.

BACKGROUND OF THE INVENTION

The present invention relates to a process for the aromatization of hydrocarbons containing between 5 and 9 carbon atoms per molecule in the presence of a composite catalyst incorporating a MFI structure zeolite containing silicon, aluminium and at least one metal from the platinum family, to which are added at least one additional metal chosen from within the group constituted by tin, germanium, indium and lead. An amorphous matrix can be added to the catalyst for the shaping thereof.

Catalysts based on zeolites doped with gallium, zinc and platinum are known to be active and selective in the aromatization of propane and butane. Conventionally hydrocarbons with more than 6 carbon atoms per molecule are transformed into aromatics by catalytic reforming using catalysts of the platinum-doped acid alumina type platinum to which can be added tin, rhenium, etc. However, these reforming catalysts do not have good performance characteristics for the aromatization of hydrocarbons with 5 carbon atoms per molecule and to a lesser extent for those with 6 carbon atoms per molecule. Thus, there is considerable interest in finding high performance catalysts for the aromatization of hydrocarbon-rich fractions of the $C_5$-$C_6$ type.

The aromatization reaction of hydrocarbons with more than 5 carbon atoms per molecule in the presence of zeolitic catalysts has already formed the subject matter of several patents and publications. Several MFI zeolite-based catalytic systems are claimed and these systems can be distinguished by the additives contained therein. A distinction can be made between:
  i) systems containing gallium (G. Berti, J. Moore, L. Salusinszki, D. Seddon, Aust. J. Chem., 42, p 2095, 1989)
  ii) systems containing zinc (O. Anunziata, O. Orio, L. Pierella, M. Aguirre, React. kin. Catal. Lett., 39(1), 75, 1989; J. Kanai, N. Kawata, J. Catal., 114, 284, 1988).

However, all these systems suffer from an important defect, namely a high methane selectivity. In order to improve the performance characteristics of these catalytic systems a number of solutions have been proposed, such as the addition of platinum (Z. Jin, Y. Makino, A. Miyamoto, T. Inui, Chem. Express, 2 p 515, 1987). The use of a non-acid MFI zeolite with various metallic elements has also been claimed (Y. Chen. et al. WO 8904818).

Moreover, in French patent application 90/06557, the Applicant claims a catalyst incorporating on the one hand a MFI zeolite and on the other a generally amorphous matrix or support, on which is deposited a noble metal from the platinum group and at least one additional metal chosen from within the group constituted by tin, germanium, indium and lead, said support also containing at least one alkali metal and at least one alkaline earth metal chosen from within the group constituted by lithium, sodium, potassium, rubidium, cesium, barium, calcium, beryllium, magnesium and strontium. This catalyst is used for the aromatization of hydrocarbons with 2 to 4 carbon atoms per molecule.

SUMMARY OF THE INVENTION

It has been found that the fixing of the noble metal from the platinum family (hydrogenating metal) and the additional metal chosen from the group constituted by tin, germanium, indium and lead, directly to the zeolite, using methods such as impregnation, exchange or any other known method have led to an improvement of the catalytic performance characteristics in the aromatization of hydrocarbons with 5 to 9 carbon atoms per molecule.

The MFI structure zeolite of said catalyst (which is preferably acid) used in the present invention can be prepared by all known methods. The synthesis of said MFI zeolite can be carried out in a conventional $OH^-$ medium, in the presence or absence of organic structuring agents and/or alcohol. The synthesis of the MFI zeolite in the $OH^-$ medium according to known methods is described in: Synthesis of High Silica Zeolites, P Jacobs and J. Martens, Studies in Surface Science and Catalysis, volume 33, Elsevier Editor, 1987. The MFI zeolite can also be synthesized in less conventional media, such as e.g. the fluoride medium (cf. our European patent EP-A-172068).

After synthesis, the MFI zeolite is transformed into a hydrogen form by the total or partial elimination of organic compounds and/or alkali metal or alkaline earth cations contained therein, possibly after synthesis. All known methods can be used for passing to the hydrogen form, such as e.g. calcination in an oxidizing or nonoxidizing atmosphere, ion exchanges followed or not by calcination, various chemical treatments, etc.

All MFI zeolites synthesized in the Si-Al system are suitable for the present invention. However, their Si/Al atomic ratio is generally higher than 7, preferably higher than 25 and more particularly between 40 and 1,000.

The hydrogenating metal is then deposited on the MFI zeolite. Any metal from group VIII of the periodic classification of elements can be used, but platinum is preferred.

The platinum can be introduced in different ways, e.g. in the form of a tetrammine complex by cationic exchange, or in the form of a hexachloroplatinic acid by impregnation.

The platinum (or optionally another noble metal from the platinum group) can consequently be incorporated into the zeolite by impregnating the latter with the aid of an adequate aqueous or nonaqueous solution containing a salt or a compound of the noble metal. The platinum is generally introduced into the zeolite in the form of chloroplatinic acid, but it is also possible to use compounds such as ammonium chloroplatinate, dicarbonyl platinum dichloride, hexahydroplatinic acid, palladium chloride and palladium nitrate.

Among the compounds of the metal or metals from the platinum group used in the present invention, reference is also made in exemplified manner to ammonium complexes.

In the case of platinum, particular reference is made to platinum IV hexaammine salts of formula $(Pt(NH_3)_6)X_4$, in which X is a halogen atom chosen from within the group formed by fluorine, chlorine, bromine and iodine and preferably X is a chlorine atom, platinum IV halopentammine salts of formula $(PtX(NH_3)_5)X_3$, platinum IV tetrahalodiammines salts of formula Pt $X_4(NH_3)_2$ in which X has the meaning given hereinbefore, complexes of platinum with halogenspolyketones and polyketone halogen compounds of formula $H(Pt(aca)_2X)$ in which X has the meaning given hereinbefore and aca represents the radical of formula $C_5H_2O_2$ derived from acetyl acetone.

The noble metal from the platinum family is preferably introduced by impregnation with the aid of an aqueous or organic solution of one of the aforementioned organometallic compounds. Among the organic solvents which can be used reference is made to paraffin, naphthene or aromatic hydrocarbons and halogen-containing organic compounds e.g. having 1 to 12 carbon atoms in their molecule. Particular reference is made to n-heptane, methyl cyclohexane, toluene and chloroform and mixtures of these solvents can also be used.

The element (or additional metal M) chosen from within the group constituted by tin, germanium, lead and indium can be introduced via compounds such as e.g. in nitrate, bromides and chlorides, halides, lead carbonate, acetate and nitrate, germanium oxalate and chloride, indium, chloride and nitrate.

The additional metal M can be introduced before or after the introduction of the nobel metal. If it is introduced before the noble metal, the compound used is chosen from the group constituted by halides, nitrates, acetates, carbonates and oxalates of the additional metal. Introduction advantageously takes place in aqueous solution. In this case, before introducing the noble metal, calcining takes place in air at a temperature between 400° and 1000° C.

The additional metal M can be introduced after the introduction of the noble metal in the from of at least one organic compound chosen from the group constituted by complexes of metals M and in particular polyketone complexes, and hydrocarbonyl metals, such as alkyl, cycloalkyl, aryl, alkyl aryl and aryl alkyl metals.

The introductions of the metal M advantageously takes place with the aid of a solution in an organic solvent of the organometallic compound of said metal M. It is also possible to use organohalogen compounds of the metals M. Compounds of metals M are in particular tetrabutyl tin, tetramethyl tin, tetrapropyl germanium, tetraethyl lead, indium acetyl acetonate and triphenyl indium.

The impregnation solution is chosen from within the group constituted by paraffin, naphthene or aromatic hydrocarbons containing 6 to 12 carbon atoms per molecule and halogen-containing organic compounds containing 1 to 12 carbon atoms per molecule. Reference is made to n-heptane, methyl cyclohexane, toluene and chloroform. It is also possible to use mixtures of the solvents defined hereinbefore.

This introduction method for the metal M has already been described in U.S. Pat. No. 4,548,918. However, the combination of the platinum family metal introduction method and the metal M introduction method produces a particular synergism.

The MFI zeolite of the catalyst used in the invention contains by weight (a) approximately 0.01 to 2 and more particularly approximately 0.1 to 0.5% of at least one noble metal from the platinum family, (b) approximately 0.005 to 0.60 and preferably 0.01 to 0.50% of tin and/or 0.005 to 0.70 and preferably approximately 0.01 to 0.60 and more particularly 0.02 to 0.50% of at least one metal chosen within the group constituted by germanium, lead and indium.

When there are at least two metals chosen from within the group constituted by tin, germanium, lead and indium, the total content of metals in said group is approximately 0.02 to 1.20, preferably 0.02 to 1.0 and more particularly 0.02 to 0.8%.

It is possible to use either a common solution of the metals which it is wished to deposit on the zeolite, or separate solutions for the metal from the platinum family and for the additional metal or metals. When several solutions are used, it is possible to carry out intermediate calcinations and/or dryings. Normally the process is completed by a calcination at e.g. between approximately 500° and 1000° C., preferably in the presence of free oxygen, e.g. by carrying out air scavenging.

Following the preparation of the catalyst, the latter is generally calcined at between 450° and 1000° C., but after calcination the catalyst can advantageously undergo an activation treatment under hydrogen and at high temperature, e.g., 300° to 500° C., in order to obtain a more active metallic phase. The procedure of this treatment under hydrogen e.g. consists of a slow temperature rise under a hydrogen stream until the maximum reduction temperature is e.g. between 300° and 500° C. and preferably between 350° and 450° C. and this is maintained for 1 to 6 hours.

This preparation procedure for the catalyst leads to a solid in which the metals are homogeneously distributed throughout the volume of the catalyst grain and are in a metallic state following the reduction treatment under hydrogen scavenging between 300° and 500° C. and maintaining for 1 to 6 hours under hydrogen at the final temperature chosen.

An advantageous method for the preparation of catalysts can involve the following stages:
(a) The MFI zeolite is impregnated with an aqueous solution of a compound of a metal chosen from within the group constituted by tin, germanium, indium and lead.
(b) The product obtained in stage (a) is dried.
(c) The product obtained in stage (b) is calcined.
(d) The product obtained in stage (c) is impregnated with a platinum acetyl acetonate solution in toluene.
(e) The product obtained in stage (d) is dried.
(f) The product obtained in stage (e) is calcined.
(g) The product obtained in stage (f) is reduced under a hydrogen stream.

Another advantageous method for the preparation of catalysts can involve the following stages:
(a) The MFI zeolite is impregnated with an aqueous solution of a compound of a metal chosen from within the group constituted by tin, indium, germanium and lead.
(b) The product obtained in stage (a) is dried.
(c) The product obtained in stage (b) is calcined.
(d) The product obtained in stage (c) is impregnated with an ammoniacal tetraammine platinum chloride solution.
(e) The product obtained in stage (d) is dried.
(f) The product obtained in stage (e) is calcined.
(g) The product obtained in stage (f) is reduced under a hydrogen stream.

Another advantageous method for the preparation of catalysts can be carried out with the following stages:
(a) The MFI zeolite is impregnated with an ammoniacal tetraammine platinum chloride solution.
(b) The product obtained in stage (a) is dried.
(c) The product obtained in stage (b) is calcined.

(d) The product obtained in stage (c) is reduced under a hydrogen stream.

(e) The product obtained in stage (d) is contacted with a hydrocarbon solvent and with said organic compound of metal M, e.g. by immersing the mass in a hydrocarbon solvent already containing the organic compound or by immersing the mass in a hydrocarbon solvent and then injecting into the mixture obtained a solution of the organic compound of said metal M in a hydrocarbon solvent and e.g. that in which said mass has been immersed.

(f) The product obtained in stage (e) is reduced under a hydrogen stream.

The catalyst can also contain a support or an amorphous matrix, e.g. chosen from among magnesium, aluminum, titanium, zirconium, thorium, silicon and boron oxides, considered singly or in mixtures. It is also possible to use carbon. The preferred support is alumina. The specific surface of the alumina is advantageously between 50 and 600 m$^2$/g and preferably between 150 and 400 m$^2$/g.

The zeolite containing the various metal described hereinbefore can be shaped with the support using any known procedure, e.g. pelletizing, extrusion, drageification, droplet coagulation, drying by atomization.

The catalyst then contains 1 to 99% by weight zeolite containing the different metals, the residue being constituted by the support or amorphous matrix.

The catalyst is used in a process for the aromatization of hydrocarbons containing 5 to 9 carbon atoms per molecule, under the conventional operating conditions for such a process. The following examples illustrate the invention without limiting its scope.

EXAMPLE 1

The aim is to transform a charge constituted by a mixture of hydrocarbons containing 5 or 6 carbon atoms in the presence of a MFI zeolite-based catalyst with a Si/Al atomic ratio of 45 containing platinum and a metal chosen from within the group constituted by tin, germanium, indium and lead.

Preparation of the MFI zeolite

The MFI zeolite is synthesized in the presence of an organic structuring agent using known formulations (U.S. Pat. No. 3,702,886). This zeolite is transformed into the H form by calcining in an air-nitrogen mixture (10% oxygen in the mixture) at 550° C. and for 4 hours, three exchanges in 5N NH$_4$NO$_3$ at 100° C. and calcining in air at 530° C. for 5 hours with a flow rate of 5 l/h/g.

The Si/Al atomic ratio of the HMFI zeolite is 45 and its porous volume measured by nitrogen adsorption at 77 K exceeds 0.160 cm$^3$/g. The metals are deposited on the MFI zeolite according to the following procedures:

Catalyst A (a) The MFI zeolite is impregnated by an aqueous tin chloride solution, so that the final tin concentration of the catalyst is 0.25% by weight.

(b) The product obtained in stage (a) is dried for 1 hour at 100° to 120° C.

(c) The product obtained in stage (b) is calcined for 2 hours at 530° C.

(d) The product obtained in stage (c) is impregnated by an aqueous hexachloroplatinic acid solution so as to obtain 0.3% platinum on the final catalyst.

(e) The product obtained is dried for 1 hour at 100° to 120° C.

(f) Calcining takes place for 2 hours at 530° C.
Catalyst A: 0.3% Pt and 0.25% Sn/MFI.

Catalyst B

The MFI zeolite is impregnated according to the same procedure as for catalyst (A), except that the tin chloride is replaced by tin acetate, the remainder of the procedure being unchanged.

Catalyst B: 0.3% Pt and 0.25% Sn/MFI.

Catalyst C

The MFI zeolite is impregnated according to the same procedure as for catalyst B, except that the platinum is impregnated by means of an ammoniacal tetraammine platinum chloride solution, the rest of the procedure being unchanged.

Catalyst C: Pt 0.3% and Sn 0.25%/MFI.

Catalyst D (comparative catalyst)

The MFI zeolite is impregnated by an ammoniacal tetraammine platinum chloride solution, so as to obtain a platinum concentration of 0.3% by weight on the final catalyst.

Catalyst D: Pt 0.3%/MFI.

EXAMPLE 2

The above-prepared catalysts were subject to an aromatization test of a C$_5$-C$_6$ fraction with the following composition (% by weight):

Paraffins
  C$_5$:90.0%
  C$_6$:54.%
Naphthenes
  C$_5$:3.7%
  C$_6$:0.9%

The operating conditions are as follows:
Temperature: 480° C.
Pressure: 0.25 megapascal
pph: 3 h$^{-1}$ The results of the comparative tests for catalysts A to D and the MFI zeolite only are given in table 1.

TABLE 1

| Catalyst | Conversion % by weight | CH$_4$ | C$_2$H$_6$ + C$_2$H$_4$ | C$_3$H$_8$ + C$_3$H$_6$ | C$_4$H$_{10}$ + C$_4$H$_8$ | Aromatics |
|---|---|---|---|---|---|---|
| MFI zeolite | 92 | 35 | 25 | 15 | 20 | 5 |
| Catalyst A | 90 | 5 | 12 | 15 | 7 | 61 |
| Catalyst B | 92 | 5 | 13 | 14 | 5 | 63 |
| Catalyst C | 94 | 4 | 10 | 12 | 8 | 66 |
| Catalyst D | 95 | 25 | 20 | 10 | 15 | 30 |

EXAMPLE 3

In order to prepare catalysts E, F and G respectively, an impregnation procedure strictly identical to that used for the preparation of catalyst C is used, except that the tin acetate is replaced by germanium oxalate (catalyst E), lead nitrate (catalyst F) and indium nitrate (catalyst G), the remainder of the procedure remaining unchanged.

Catalyst E: Pt=0.3% and Ge 0.20%/MFI
Catalyst F: Pt=0.3% and Pb 0.35%/MFI
Catalyst G: Pt=0.3% and In 0.25%/MFI Table 2 gives the results of the aromatization tests for the C$_5$-C$_6$ fraction performed with these catalysts under the same conditions as defined in example 2.

TABLE 2

| Catalyst | Conversion % by weight | Selectivity (% by weight) | | | | |
|---|---|---|---|---|---|---|
| | | $CH_4$ | $C_2H_6$ + $C_2H_4$ | $C_3H_8$ + $C_3H_6$ | $C_4H_{10}$ + $C_4H_8$ | Aromatics |
| Catalyst D | 95 | 25 | 20 | 10 | 15 | 30 |
| Catalyst E | 90 | 5 | 13 | 14 | 4 | 64 |
| Catalyst F | 91 | 5 | 11 | 16 | 5 | 63 |
| Catalyst G | 93 | 5 | 12 | 15 | 6 | 62 |
| Catalyst C | 94 | 4 | 10 | 12 | 8 | 66 |

EXAMPLE 4

The above-prepared catalyst D is reduced under a hydrogen stream for 2 hours at 450° C. 100 g of this catalyst are immersed in 300 cm³ of n-heptane. Into the catalyst-containing n-heptane are then injected 2 g of a tetra n-butyl tin solution in n-heptane (10% tin). The contact between the platinum catalyst and the tetra n-butyl tin solution is maintained for 6 hours at the reflux temperature of the heptane. The impregnation solution is then discharged and three washing operations are carried out with pure n-heptane at the reflux temperature of the n-heptane. The catalyst is then dried. It can then undergo either a calcination in air for 2 hours at 500° C. and followed by a reduction under a hydrogen stream at 450° C. and for 2 hours before being introduced into the reactor, or undergo a direct reduction under a hydrogen stream at 450° C. for 2 hours before being fed into the reactor.

This gives catalyst H: Pt: 0.3% and Sn: 0.2%/MFI.

The aromatization results with respect to the $C_5$-$C_6$ fraction under conditions identical to those of example 2 are given in table 3.

TABLE 3

| Catalyst | Conversion % by weight | Selectivity (% by weight) | | | | |
|---|---|---|---|---|---|---|
| | | $CH_4$ | $C_2H_6$ + $C_2H_4$ | $C_3H_8$ + $C_3H_6$ | $C_4H_{10}$ + $C_4H_8$ | Aromatics |
| Catalyst D | 95 | 25 | 20 | 10 | 15 | 30 |
| Catalyst C | 94 | 4 | 10 | 12 | 8 | 66 |
| Catalyst H | 95 | 4 | 8 | 10 | 8 | 70 |

Thus, a good aromatic product selectivity is obtained with the catalysts in accordance with those used in the present invention (A, B, C, E, F, G and H).

We claim:

1. In a process for the aromatization of hydrocarbons containing 5 to 9 carbon atoms per molecule, the improvement comprising conducting the aromatization in the presence of at least one zeolite-containing catalyst, said zeolite having the structure of an MFI zeolite and synthesized from a system containing essentially of Si/Al, and wherein metals consisting essentially of at least one noble metal from the platinum family and at least one additional metal selected from the group consisting of tin, germanium, lead and indium are incorporated onto said MFI zeolite.

2. Process according to claim 1, wherein said metals consist essentially of at least one noble metal from the platinum family in a quantity of approximately 0.1 to 2% by weight and said at least one additional metal is selected from the group consisting of tin, germanium, lead and indium in a quantity of approximately 0.005 to 0.60% by weight for the tin and a quantity of approximately 0.005 to 0.70% by weight for the germanium, lead or indium.

3. Process according to claim 1, wherein said metals consist essentially of at least one noble metal from the platinum family in a quantity of approximately 0.1 to 0.5% by weight and at least one additional metal selected from the group consisting of tin, germanium, lead and indium in a quantity of approximately 0.01 to 0.50% by weight for the tin and in a quantity of approximately 0.01 to 0.60% by weight for the germanium, lead or indium.

4. Process according to wherein said additional metals consist essentially of tin and at least one metal selected from the group consisting of germanium, lead and indium, the total additional metal content of said zeolite being approximately 0.02 to 1.20% by weight.

5. Process according to claim 1, wherein the catalyst also contains a matrix.

6. Process according to claim 5 wherein the catalyst contain by weight 1 to 99% of said zeolite and 99 to 1% of said matrix.

7. Process according to claim 5, wherein said matrix is alumina.

8. Process for the aromatization of hydrocarbons according to claim 1, wherein said additional metals consist essentially of tin and at least one metal selected from the group consisting of germanium, lead and indium.

9. Process according to claim 2, wherein said additional metals consist essentially of tin and at least one metal selected from the group consisting of germanium, lead and indium, the total additional metal content of said zeolite being approximately 0.02 to 1.20% by weight.

10. Process according to claim 8, wherein said additional metals consist essentially of tin and at least one metal selected from the group consisting of germanium, lead and indium, the total additional metal content of said zeolite being approximately 0.02 to 1.20% by weight.

11. Process according to claim 10, wherein the catalyst also contains a matrix.

12. Process according to claim 11 wherein the catalyst consists essentially of, by weight, 1 to 99% of said zeolite and 99 to 1% of said matrix.

13. Process according to claim 12, wherein said matrix is alumina.

14. A process according to claim 1, wherein the incorporated metals are platinum and tin.

* * * * *